United States Patent
Webber

(10) Patent No.: US 11,754,858 B2
(45) Date of Patent: Sep. 12, 2023

(54) MULTIFOCAL OPHTHALMIC LENS AND RELATED METHODS

(71) Applicant: CooperVision International Limited, Fareham (GB)

(72) Inventor: Martin Webber, Southampton (GB)

(73) Assignee: COOPERVISION INTERNATIONAL LIMITED, Fareham (GB)

( * ) Notice: Subject to any disclaimer, the term of this patent is extended or adjusted under 35 U.S.C. 154(b) by 248 days.

(21) Appl. No.: 17/228,752

(22) Filed: Apr. 13, 2021

(65) Prior Publication Data

US 2021/0341755 A1    Nov. 4, 2021

Related U.S. Application Data

(60) Provisional application No. 63/017,931, filed on Apr. 30, 2020.

(51) Int. Cl.
*G02C 7/02* (2006.01)
*G02C 7/04* (2006.01)

(52) U.S. Cl.
CPC ............ *G02C 7/044* (2013.01); *G02C 7/027* (2013.01); *G02C 2202/20* (2013.01)

(58) Field of Classification Search
CPC .... G02C 7/044; G02C 7/027; G02C 2202/20; G02C 2202/24; G02C 7/06; G02C 7/042; G02C 7/02; G02C 7/022; G02C 7/04; G02C 7/041; A61F 2/1618; B29D 11/00038; G02B 1/043
USPC ................................. 351/41, 159.1, 159.41
See application file for complete search history.

(56) References Cited

U.S. PATENT DOCUMENTS

| 7,766,478 | B2 | 8/2010 | Phillips |
| 7,832,859 | B2 | 11/2010 | Phillips |
| 8,240,847 | B2 | 8/2012 | Holden et al. |
| 8,950,860 | B2 | 2/2015 | Tse et al. |
| 9,594,259 | B2 | 3/2017 | Brennan et al. |
| 9,829,722 | B2 | 11/2017 | Tse et al. |
| RE47,006 | E | 8/2018 | To et al. |

(Continued)

FOREIGN PATENT DOCUMENTS

| EP | 0622653 A1 | 11/1994 |
| EP | 2761359 A1 | 8/2014 |

(Continued)

OTHER PUBLICATIONS

International Search Report and Written Opinion issued in corresponding International Patent Application No. PCT/GB2021/051038 dated Aug. 6, 2021 (15 pages).

(Continued)

*Primary Examiner* — Tuyen Tra
(74) *Attorney, Agent, or Firm* — Kilyk & Bowersox, P.L.L.C.

(57) ABSTRACT

A multifocal ophthalmic lens has a surface that varies across at least a portion of the lens to form a surface power map. The surface power map comprises a spiral, with a power that varies substantially periodically both radially outwards from and angularly about an optical axis of the lens. A period of the radial variation is greater than 100 microns and a period of the angular variation is greater than 6 degrees. Methods of making and using the multifocal ophthalmic lens are also described.

16 Claims, 6 Drawing Sheets

(56) References Cited

U.S. PATENT DOCUMENTS

| | | |
|---|---|---|
| 10,061,143 B2 | 8/2018 | Brennan et al. |
| 10,268,050 B2 | 4/2019 | To et al. |
| 10,416,476 B2 | 9/2019 | Lin et al. |
| 10,429,670 B2 | 10/2019 | Newman |
| 2003/0117577 A1 | 6/2003 | Jones et al. |
| 2007/0091260 A1* | 4/2007 | Guillon .................. G02C 7/081 |
| | | 351/159.05 |
| 2011/0234974 A1* | 9/2011 | Lawu ....................... G02C 7/06 |
| | | 623/6.11 |
| 2014/0211313 A1 | 7/2014 | Dobschal |
| 2014/0293426 A1 | 10/2014 | Dobschal |
| 2016/0377884 A1 | 12/2016 | Lau et al. |
| 2017/0115509 A1 | 4/2017 | Brennan et al. |
| 2018/0275427 A1 | 9/2018 | Lau et al. |
| 2019/0212580 A1 | 7/2019 | To et al. |

FOREIGN PATENT DOCUMENTS

| | | |
|---|---|---|
| WO | 9526518 A1 | 10/1995 |
| WO | 2009012789 A1 | 1/2009 |
| WO | 2012156081 A1 | 11/2012 |
| WO | 2013001299 A1 | 1/2013 |
| WO | 2015004881 A1 | 1/2015 |
| WO | 2016161351 A1 | 10/2016 |
| WO | 2020260679 A1 | 12/2020 |

OTHER PUBLICATIONS

Search Report issued in corresponding United Kingdom Patent Application No. GB2106174.2 dated Oct. 6, 2021 (4 pages).
U.S. Appl. No. 17/228,755, filed Apr. 13, 2021 (42 pages).
U.S. Appl. No. 17/228,757, filed Apr. 13, 2021 (45 pages).

* cited by examiner

MULTIFOCAL OPHTHALMIC LENS AND RELATED METHODS

This application claims the benefit under 35 U.S.C. § 119(e) of prior U.S. Provisional Patent Application No. 63/017,931, filed Apr. 30, 2020, which is incorporated in its entirety by reference herein.

TECHNICAL FIELD

The present invention concerns multifocal ophthalmic lenses. More particularly, but not exclusively, this invention concerns a multifocal ophthalmic lens having a spiral surface power map, as well as methods of making such lenses, and methods of using such lenses.

BACKGROUND

In the context of the present disclosure, a multifocal ophthalmic lens is an ophthalmic lens which simultaneously provides focussing to more than one distance. This is typically achieved by subdividing the ophthalmic lens into a plurality of regions. A first subset of the plurality of regions are provided with a first lens power, corresponding to a first focussing distance (for example distance vision). A second subset of the plurality of regions are provided with a second lens power, corresponding to a second focussing distance (for example near vision).

In multifocal contact lenses, the plurality of regions can be formed as concentric circles centred on the optical axis of the contact lens, with the concentric circles alternating between the first lens power and the second lens power. Thus, in this example, the power map or power profile of an optic zone of a typical multifocal contact lens comprises at least two alternating concentric circles of a first lens power and a second lens power. However, such contact lenses can cause difficulties for wearers in changeable light conditions. In lower light conditions, the pupil of the wearer's eye dilates in order to provide a larger aperture for incident light, increasing the amount of light received into the eye and thereby providing improved low-light vision. As conditions brighten, the pupil constricts to provide a smaller aperture and thereby limit the amount of light received into the eye. As the wearer's pupil dilates and constricts, the number of the concentric rings on the contact lens which are positioned across the wearer's entrance pupil will also vary. As the pupil dilates, a greater number of the concentric rings will be positioned across the wearer's entrance pupil. Likewise, as the pupil constricts, fewer of the concentric rings will be positioned across the wearer's entrance pupil. Because the concentric rings alternate between the first lens power and the second lens power, the ratio of the first lens power to the second lens power positioned across the wearer's entrance pupil will vary as the wearer's pupil constricts and dilates. As the pupil constricts, the quantity of only one of near and distance focussing is reduced until the pupil has constricted to the diameter of the next smallest concentric circle. At this point, the quantity of only the other of the near and distance focussing is reduced until the pupil has constricted to the diameter of the next smallest concentric circle again. This cycle repeats as the pupil constricts, causing variation in the ratio of the near focussing to the distance focussing as the pupil constricts. It will be appreciated that the same effect occurs in reverse as the pupil dilates. These variations in the ratio of near to distance focussing can cause distraction to the wearer and even a loss of multifocal vision. Generally, the more constricted the wearer's pupil, the more exacerbated this variation in the ratio. Therefore, in bright conditions in particular, when the pupil constricts to near to its minimum size, wearers of such multifocal contact lenses may find that the ability of the multifocal contact lens to provide high acuity in both near and distance vision is impaired. This effect is exacerbated further for two-zone multifocal contact lenses, which are one of the more prevalent designs of multifocal contact lens. Two-zone multifocal contact lenses comprise an inner circle of a first lens power and a single surrounding peripheral ring of a second lens power. Thus, the more the pupil of a wearer of such a contact lens constricts, the less of the second lens power is positioned across the wearer's entrance pupil. In some cases, the pupil may even constrict to the extent that none of the second lens power is positioned across the wearer's entrance pupil, causing a complete loss of multifocal vision. Other multifocal contact lenses utilise a similar principle but, instead of alternating concentric rings, include an aspheric power profile to provide a more gradual transition from near viewing powers to distance viewing powers compared to lenses incorporating alternating concentric rings. Such lenses also suffer from variation in the ratio of lens powers positioned across the wearer's entrance pupil as the wearer's pupil dilates and constricts.

The present invention seeks to mitigate the above-mentioned problems. Alternatively or additionally, the present invention seeks to provide an improved multifocal ophthalmic lens.

SUMMARY

The present invention provides, according to a first aspect, a multifocal ophthalmic lens. A surface of the ophthalmic lens varies across at least a portion of the lens to form a surface power map. The surface power map comprises a spiral, with a power that varies substantially periodically both radially outwards from and angularly about an optical axis of the lens. A period of the radial variation is greater than 100 microns and a period of the angular variation is greater than 6 degrees.

A contact lens having a surface power map comprising a spiral can provide a more stable ratio of near vision focussing to distance vision focussing in the presence of changes in the pupil size of the wearer. As light conditions change, the wearer's pupil will dilate and constrict in order to regulate the amount of light received into the eye. As conditions brighten, the pupil constricts to reduce the amount of light allowed into the eye. As conditions darken, the pupil dilates to allow more light into the eye. Multifocal contact lenses of the prior art may use alternating concentric rings of near and distance focussing, for example a central circle of distance focussing surrounded by a peripheral circle of near focussing, or existing multifocal contact lenses may use an aspheric power profile to provide multifocal vision. As discussed above, these contact lenses suffer from variation in the ratio of near focussing to distance focussing provided across the wearer's entrance pupil as the wearer's pupil dilates and constricts. These variations can cause distraction to the wearer and even a loss of multifocal vision.

A spiral power map has a constant ratio of near focussing to distance focussing across the full range of diameters including the spiral map. Thus, a contact lens having a spiral power map can maintain either a substantially constant ratio (where the spiral cover the whole of the optic zone of the lens) or a monotonically varying ratio (where the spiral covers only a radial sub-portion of the optic zone of the lens) of near to distance focussing as the pupil constricts or dilates. Thus, a contact lens having a spiral power map provides improved multiple focussing in the presence of variable lighting conditions.

It will be appreciated by the skilled person that, where the power map varies smoothly (for example, as a sinusoid), the power map will comprise lens powers other than simply a first lens power corresponding to near vision and a second lens power corresponding to distance vision. In such a case, the power map will also comprise regions having lens powers between the first and second powers. It will be appreciated that this does not affect or diminish the advantage described above of providing a consistent and stable variation in the add power positioned across the wearer's entrance pupil. It will be appreciated by the skilled person that this advantage is derived from that fact that, for a spiral power map, the composition of add powers at a particular radius does not vary according to a radial distance from the optical axis of the lens.

According to a second aspect of the invention there is also provided a method of manufacturing a multifocal ophthalmic lens. The method comprises operating a lathe to shape a surface of at least one of: a lens, a mould for a lens, or an insert for manufacturing a mould for a lens. At least a portion of the surface is shaped such that it forms a power map comprising a spiral. The power map varies substantially periodically both radially outwards from and angularly about an optical axis of the lens. A period of the radial variation is greater than 100 microns and a period of each of the angular variation is greater than 6 degrees.

According to a third aspect of the invention there is also provided a method of using the multifocal ophthalmic lens described herein. The methods may be effective in improving the vision of a presbyopic lens wearer (e.g., a person 40 years old or older). Or, alternatively, the methods may be effective in reducing progression of a refractive error, such as reducing the progression of myopia or hyperopia. When the present lenses are used to reduce the progression of myopia, the methods include a step of providing the ophthalmic lenses to a person whose eyes are able to accommodate. Some embodiments of the methods include a step of providing the ophthalmic lenses to a person that is from about 5 years old to about 18 years old. The providing can be performed by an eye care practitioner, such as an optician or optometrist. Alternately, the providing can be performed by a lens distributor that arranges for the delivery of the ophthalmic lenses to the lens wearer.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which.

DETAILED DESCRIPTION

Figure 1:
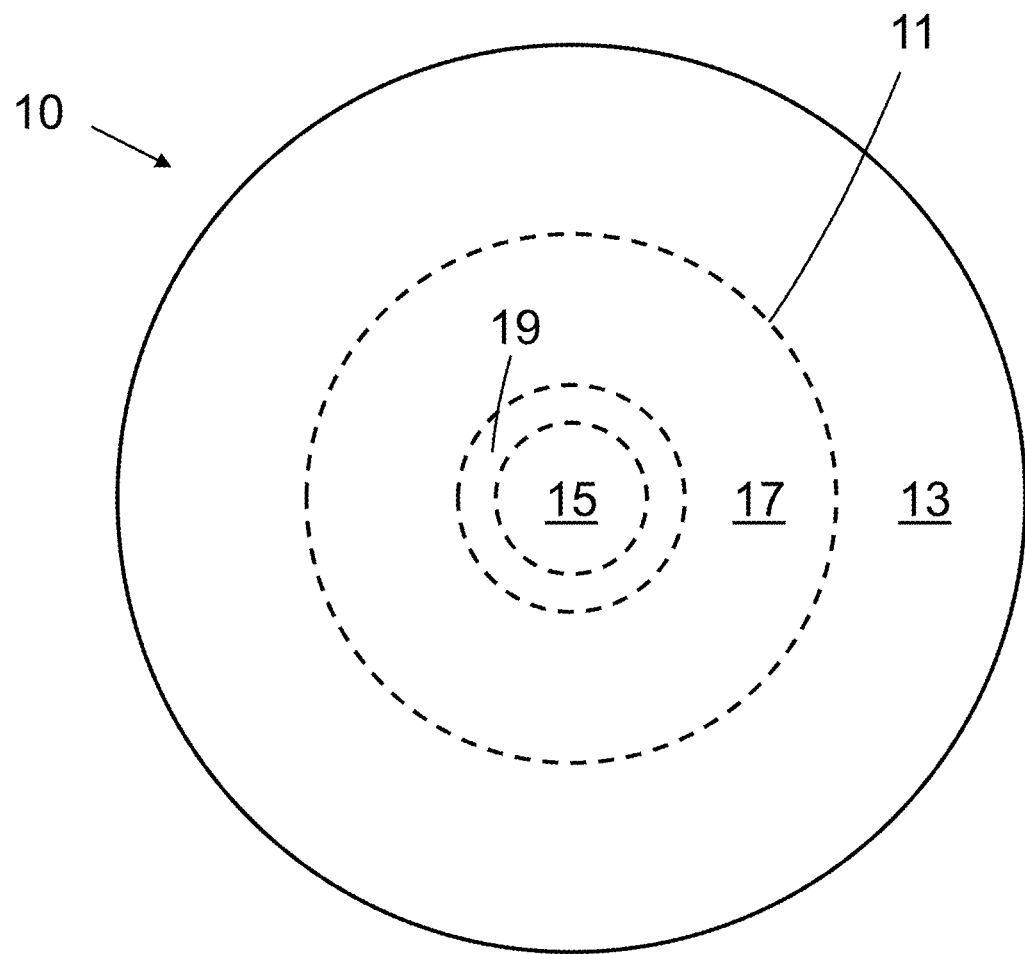
FIG. 1 shows a contact lens according to embodiments of the invention.

The present invention provides, according to the first aspect, a multifocal ophthalmic lens. A surface of the ophthalmic lens varies across at least a portion of the lens to form a surface power map. It will therefore be appreciated by the skilled person that the variation of the surface comprises a variation in the curvature of the lens surface. The surface power map comprises a spiral, with a power that varies substantially periodically both radially outwards from and angularly about an optical axis of the lens. A period of the radial variation is greater than 100 microns and a period of the angular variation is greater than 6 degrees.

It may be that the ophthalmic lens is a contact lens. It may be that the first surface varies across an optic zone of the contact lens to form the first surface power map. Thus, it may be that the portion of the lens corresponds to an optic zone of the lens. Alternatively, the ophthalmic lens may be an intraocular lens or a spectacle lens.

In the case of contact lenses, it will be appreciated that the lens will comprise an optic zone, which provides vision modification. Contact lenses according to embodiments of the invention may also comprise a surrounding peripheral zone, which provides no additional focussing or vision modification. In such embodiments, the peripheral zone may serve merely to help maintain the contact lens in position on the wearer's eye. Thus, it will be appreciated by the skilled person that the surface power map is defined by the variation of the first surface across the optic zone of the lens. Variation of the lens surface outside of the optic zone (for example, in a peripheral zone) is not, in the context of the present invention, to be treated as defining the surface power map. Similar considerations also apply to intraocular lenses, which may also comprise an optic zone and (optionally) a peripheral zone.

It may be that the optic zone of a contact lens according to embodiments of the present invention has a diameter of between 4 mm and 9 mm, depending on the type of contact lens. For example, the diameter of the optic zone may be about 5 mm, or about 6 mm, or about 7 mm, or about 8 mm. In some embodiments, the diameter of the optic zone of the contact lens is between 7 mm and 9 mm. The optic zone includes an optical axis that corresponds to the geometric centre of the optic zone.

In the case of spectacle lenses, the entire lens may serve to provide vision correction, rather than just a portion of the lens. Thus, the ophthalmic lens may be a spectacle lens. It may be that the first surface varies across the whole of the lens to form the first surface power map.

It may be that one or both of the radial and angular variations are of constant magnitude across the portion.

It may be that the period of the radial variation is greater than 200 microns, preferably greater than 400 microns, and more preferably greater than 800 microns. It may be that a period of the angular variation is greater than 6 degrees, preferably greater than 9 degrees, more preferably greater than 18 degrees, and yet more preferably greater than 36 degrees.

It may be that the power varies smoothly across the portion. It may be that power varies continuously, without any discontinuities. It may be that the power varies across the portion at a rate of less than 80 D/mm, preferably less than 40 D/mm, more preferably less than 20 D/mm. It may be that the surface varies smoothly across the portion. It may be that surface varies continuously, without any discontinuities. Varying the power smoothly can result in a lens surface profile which is easier to manufacture using a lathe. It will be appreciated by the skilled person that manufacturing an ophthalmic lens using a lathe may comprise using a lathe to shape a surface of one or more of a lens (for example a contact lens), a mould for a lens (for example a mould for a contact lens), and an insert for a lens mould (for example an insert for a contact lens mould). Sharp transitions and features can be difficult to achieve using a lathe. Therefore, lenses having such features are often not be reproducible with the intended or required definition when manufactured using a lathe. Thus, it will also be appreciated that the term smoothly in this context means smooth enough to enable the desired shaping of the surface of a lens, a mould for a lens, or an insert for a lens mould using a lathe.

The power may vary as a square wave in one or both of the radial and angular directions. The power may vary as a rounded square wave in one or both of the radial and angular directions. The power may vary as a sinusoid in one or both of the radial and angular directions.

It may be that the power variation in each of the radial and angular directions is associated with a respective waveform. In addition, a power distribution of the waveforms may be symmetrical with a substantially equal balance between near vision correction and distance vision correction. Alternately, the power distribution may be biased towards either distance vision correction or near vision correction. Thus, the power distributions of the waveforms may be asymmetric in one of the radial direction and the angular direction, or both.

The period of one or both of the radial and angular variations may be substantially constant across the portion of the lens. Embodiments of the invention in which the radial and angular variations are substantially constant yield a lens surface profile which is easier to manufacture using a lathe compared to embodiments in which the radial and angular variations are not constant. In a contact lens according to embodiments of the present invention, one or both of the radial variations and angular variations may be substantially constant from a perimeter of the optic zone in toward the optical axis of the optic zone.

The period of one or both of the radial and angular variations may change according to either or both of a radial distance from optical axis of the lens and an angular position about the optical axis. Embodiments of the invention in which the period of one or both of the radial and angular variations change according to position on the lens can provide a lens in which the characteristics of the spiral (for example its rate of rotation or arm width) differ in different regions of the lens.

Changes in the period of the radial variation may be separated by a blending region, for example of linearly varying lens power. The blending region may, therefore, comprise a concentric ring of linearly varying lens power between a first region having a first period of radial variation and a second region having a second period of radial variation. Thus, the blending region may provide a smooth transition between regions of different period radial variation. It may be that regions of different period radial variation are separated by two blending regions and an intervening region of substantially constant lens power. The blending region may have a width (in plan view) from about 25 micrometers to about 200 micrometers.

The period of the angular variation may be less than 180, preferably less than 90, more preferably less than 45 degrees. The spiral may comprise more than two arms, preferably more than 4 arms, more preferably more than 8 arms. It will be appreciated by a person skilled in the art that the period of the angular sinusoidal variation determines the number of arms on the spiral.

The period of the radial variation may be between 24 mm and 2 mm. The period of the radial variation may be between 16 mm and 4 mm. It may be that each arm of the spiral twists through between a quarter of a rotation and 40 rotations. It will be appreciated by a person skilled in the art that the number of rotations that an arm of the spiral twists through is determined by the period of the radial variation and a radius (or size) of the portion of the lens. It will be appreciated that references to the radius of the portion (for example, an optic zone of a contact lens) refer to a distance of half of a plan view diameter of the portion. In this context, a plan view is intended to taken as a view along the optical axis of the lens.

It may be that a ratio of the period of the radial variation to that of the angular variation is greater than 0.1 mm:6°. It may be that each arm of the spiral is wider than 0.1 mm, preferably wider than 0.5 mm, more preferably wider than 1 mm. The width of the spiral arms are determined when viewing the power map in plan view (i.e. along the optical axis of the lens), as shown in the accompanying drawings. It will be understood by a person skilled in the art that a width of an arm at a given radius is defined as its perpendicular width (i.e. its width in the direction perpendicular to the given radius). The width of the arm is, in this context, defined as the distance between two points immediately adjacent each side of the arm, both points having either a maximum or a minimum gradient, between which the power undergoes a single positive or negative excursion. The skilled person will appreciate that such a definition of width provides a straight line measurement of arm width along a tangent to a circle of the given radius. The skilled person will further appreciate that a measurement of width under this definition will differ from a measurement of the width of an arm taken as an arc of a circle having the given radius. Unlike a width measurement under the straight-line width definition, such an arc-based measurement would be proportional to the angular period. The magnitude of the difference between the widths obtained by these two methods will depend on the angular period in the particular case at hand.

It may be that each arm of the spiral extends from the centre of the portion of the lens to the periphery of the portion. Embodiments of the invention in which the arms of the spiral extend from the centre of the portion of a contact lens to the periphery of the portion can provide a substantially constant ratio of the first lens power to the second lens power in the presence of varying pupil dilation. Such embodiments thereby provide high acuity multifocal vision in a wide range of light conditions.

The portion of the lens may comprise a central region and an outer region. The central region may immediately surround the optical axis of the lens. The outer region may immediately surround the central region. It may be that the power of the central region does not vary periodically across the central region. The outer region may comprise the angular and radial variations in power. Providing a contact lens having an optic zone with a central region having a lens power corresponding to distance vision and free from periodic power variation can ensure that the wearer maintains high acuity distance vision even in bright conditions. For example, this may be particularly advantageous to the wearer when driving.

A contact lens according to an embodiment of the invention may include a surrounding peripheral zone, which provides no additional focussing or vision correction and serves merely to help maintain the contact lens in position on the wearer's eye. When worn on an eye, the contact lens rests on the cornea and the optic zone approximately covers the pupil of the wearer, in the conventional manner. Thus, the diameter of the central region may be less than 50%, preferably less than 40%, more preferably less than 30%, of that of the optic zone. The central region may be smaller than the minimum pupil size of a wearer of the contact lens. Such embodiments of the invention can provide a central region which is smaller than the minimum pupil size of the wearer. Embodiments of the invention having a central region which is smaller than the minimum pupil size of the wearer can maintain high acuity near vision and distance vision in the presence of varying light conditions.

The power of the central region may be substantially constant (for example, the power may vary by less than 0.25 diopters (D) from a nominal power of the central region). The central region may have a lens power corresponding to distance vision. Contact lenses according to embodiments of the invention in which the central region has a substantially constant lens power corresponding to distance vision can provide high acuity distance vision in bright light conditions, when the pupil is at its minimum size. High acuity distance vision is generally more useful to the wearer than high acuity near vision in bright light conditions because such conditions generally correspond to daytime outdoor environments when the wearer typically has greater need for distance vision than for near vision. Alternatively, the central region may have a lens power corresponding to near vision. Furthermore, the central region may have a lens power that is more positive than the near vision correction power required by the lens wearer. For example, the power of the central region may be +0.25 D to +1.25 D more positive than required by an eye for near vision correction.

The lens may comprise a transition region. The transition region may surround the central region. The outer region may surround the transition region. It may be that the power of the transition region varies to provide a smooth transition between the central and outer regions. Embodiments of the invention providing a smooth transition between the central and outer regions can enable easier manufacture using a lathe of a lens, a mould for such a lens, or an insert for such a lens mould. Thus, it will be appreciated by the skilled person that smooth in this context means that the lens profile must be smooth enough to be produced using a lathe.

The lens may comprise a second surface forming a second surface power map. The second surface may be an opposing surface to the first surface of the ophthalmic lens. It may be that the second surface power map does not vary periodically across the portion of the lens. Thus, the portion as a whole may have a spiral lens power map. Contact lenses according to embodiments of the invention in which the optic zone comprises a spiral lens power map can provide a substantially constant ratio of the first lens power to the second lens power in the presence of varying pupil size.

It will be appreciated that the second surface power map may have a substantially constant power of +0 D across the power map. For the purposes of this description, the second surface of the lens is still considered to form a second surface power map, even though that second surface power map ultimately provides no focussing or vision modification.

The second surface power map may vary substantially periodically radially outwards from the centre of the portion. A period of the radial variation of the second surface may greater than 100 microns, preferably greater than 200 microns, more preferably greater than 400 microns, and yet more preferably greater than 800 microns.

The second surface power map may vary substantially periodically angularly about the optical axis of the lens. A period of the angular variation of the second surface may be greater than 6 degrees, preferably greater than 9 degrees, more preferably greater than 18 degrees, and yet more preferably greater than 36 degrees.

Thus, in embodiments, it may be that the radial variation has a period of greater than 100 microns and the angular variation has a period of greater than 6 degrees, preferably greater than 9 degrees, more preferably greater than 18 degrees, and yet more preferably greater than 36 degrees. In other embodiments, it may be that the radial variation has a period of greater than 200 microns and the angular variation has a period of greater than 6 degrees, preferably greater than 9 degrees, more preferably greater than 18 degrees, and yet more preferably greater than 36 degrees. In other embodiments, it may be that the radial variation has a period of greater than 400 microns and the angular variation has a period of greater than 6 degrees, preferably greater than 9 degrees, more preferably greater than 18 degrees, and yet more preferably greater than 36 degrees. In other embodiments, it may be that the radial variation has a period of greater than 800 microns and the angular variation has a period of greater than 6 degrees, preferably greater than 9 degrees, more preferably greater than 18 degrees, and yet more preferably greater than 36 degrees.

The periods and phases of the radial and angular variations of the second surface may be the same as those of the first surface. The second surface power map may therefore also comprise a spiral, for example a spiral matching that of the first surface. In such embodiments, the power map of the lens as a whole also comprises a spiral. Embodiments of the invention comprising contact lenses with a spiral lens power map can provide substantially a substantially constant ratio of the first lens power to the second lens power in the presence of varying pupil size.

The power maps formed on the first and second surfaces may each comprise a spiral. It may be that the spirals provided by the first and second surfaces twist in opposing directions. Thus, the first and second surface power maps can be said to comprise counter-rotating spirals. The spirals provided by the first and second surface power maps may be the same but for the opposing twist directions. Embodiments of the invention in which the first and second surface power maps comprise counter-rotating spirals can give a lens power map which approximates a dartboard-like pattern of alternating annular rings. It will be appreciated by a person skilled in the art that the lens power map is formed by the superposition of the power maps of each of the first and second surfaces. Thus, it will also be appreciated that the pseudo-dartboard pattern is provided by the combination of the first and second surface power maps, each of which retains the previously described benefits of ease of manufacture. Thus, such embodiments can enable easier manufacture of a lens having a pseudo-dartboard power map using a lathe.

The lens power map may comprise a plurality of sections. The plurality of sections may provide either a first power corresponding to distance vision or a second power corresponding to near vision. Accordingly, the first power may be between 0 diopters (D) and −10 D. In some embodiments, the first power is from −0.25 D to −6.00 D. The second power provided in the present lenses may be more positive than the first power of the lens, for example, the second power may be from 1 D to 5 D more positive than the first power. In some embodiments, the second power may be 1 D to 4 D more positive than the first power. In further embodiments, the second power may be 2 D to 3 D more positive than the first power. And, in some embodiments, the second power may vary, such as may occur when providing discrete segments of defocus with more positive power than the first power, such that some of the segments may have a second power of +1 D, some segments may have a second power of +2 D, and some segments may have a second power of +3 D. The variation of the second power may occur within the same arm, or may occur in different arms. The zones may be arranged on the lens such that they alternate radially and/or angularly between the first power and the second power.

The multifocal lens may be a myopia control lens. Thus, the multifocal lens may be configured to reduce the progression of myopia in a person whose eyes are able to accommodate. The multifocal lens may be suitable for correcting presbyopia. Thus, the multifocal lens may be configured to provide distance vision correction and near vision correction to a person whose eyes are unable to accommodate sufficiently (e.g., a person 40 years old or greater). The plurality of zones may provide either a power corresponding to high acuity distance vision or a power corresponding to high acuity near vision. The zones may be arranged on the lens such that they alternate radially and/or angularly between high acuity near and distance vision.

A contact lens according to an embodiment of the invention may comprise a ballast to orient the lens when positioned on the eye of a wearer. Such a ballast may be provided by a peripheral zone of the contact lens. In certain embodiments of the invention, it may be that the contact lens provides particular benefit to the wearer in a given orientation. Embodiments of the invention incorporating a ballast into the contact lens will, when placed on the eye of a wearer, rotate under the action of the wearer's eyelid to a pre-determined angle of repose; for example the ballast may be a wedge and the rotation may result from the action of the eyelid on the wedge. By positioning the ballast in the contact lens, it is possible to ensure that the angle of repose corresponds to a lens orientation providing particular benefit to the wearer.

The present invention provides, according to the second aspect, a method of manufacturing a multifocal ophthalmic lens (for example a contact lens). The method comprises operating a lathe to shape a first surface of one of: a lens (for example a contact lens), a mould for a lens (for example a mould for a contact lens), or an insert for manufacturing a mould for a lens (for example an insert for a mould for a contact lens). The first surface is shaped to vary across at least a portion of the lens to form a first surface power map comprising a spiral. The first surface is shaped such that the surface power map varies substantially periodically both radially outwards from and angularly about an optical axis of the lens. A period of the radial variation is greater than 100 microns. A period of each of the angular variation is greater than 6 degrees.

It may be that the method comprises operating a lathe to shape the surface of at least a portion of a lens. Alternatively or additionally, the method may comprise operating a lathe to shape the surface of at least a portion of a mould for a lens.

Alternatively or additionally, the method may comprise operating a lathe to shape the surface of at least a portion of an insert for manufacturing of a mould for a lens. It will be appreciated by the skilled person that the further removed the subject of the shaping by the lathe is from the lens, the less feature definition that will be reproduced on the resulting lens. Thus, for example, shaping the surface of a lens using a lathe enables more defined surface features than will be achievable when using the lathe to shape the surface of a mould for a lens. The method may further comprise operating a lathe to shape a second surface of the lens, the mould, or the insert. The second surface may be shaped to vary across at least the portion of the lens to form a second surface power map comprising a spiral. The second surface may be shaped such that the second surface power map varies substantially periodically both radially outwards from and angularly about an optical axis of the lens. A period of the radial variation may be greater than 100 microns. A period of the angular variation may be greater than 6 degrees. The second surface may be shaped such that the second surface power map varies as a mirror image of the first surface. The second surface may be shaped such that the spiral formed by the first surface power map twists in the opposite direction to that formed by the second surface power map.

It may be that the lens is a contact lens. In such embodiments, the portion of the lens may correspond to an optic zone of the contact lens. In such cases, it will be appreciated that references to an optic zone of a mould or an insert for a mould refer to the part of the mould which corresponds to the optic zone of a lens manufactured using that mould or insert.

Lenses, for example contact lenses, according to the present invention can be formed by cast moulding processes, spin cast moulding processes, or lathing processes, or a combination thereof. As understood by persons skilled in the art, cast moulding refers to the moulding of a lens member by placing a lens forming material between a female mould member having a concave lens member forming surface, and a male mould member having a convex lens member forming surface.

In embodiments in which the ophthalmic lens comprises a contact lens, the contact lens material, as it is used as a part of a contact lens or as an entire contact lens, is visually transparent (although it can include a handling tint). The contact lens material can be a hydrogel material, a silicone hydrogel material, or a silicone elastomer material, as understood in the art. In other words, the present contact lenses can comprise, consist essentially of, or consist of a hydrogel material, a silicone hydrogel material, or a silicone elastomer material. As understood in the field of contact lenses, a hydrogel is a material that retains water in an equilibrium state and is free of a silicone-containing chemical. A silicone hydrogel is a hydrogel that includes a silicone-containing chemical. Hydrogel materials and silicone hydrogel materials, as used herein, have an equilibrium water content (EWC) of at least 10% to about 90% (wt/wt). In some embodiments, the hydrogel material or silicone hydrogel material has an EWC from about 30% to about 70% (wt/wt). In comparison, a silicone elastomer material, as used herein, has a water content from about 0% to less than 10% (wt/wt). Typically, the silicone elastomer materials used with the present methods or apparatus have a water content from 0.1% to 3% (wt/wt). Alternatively, examples of the present contact lenses can be made from rigid gas permeable materials, such as polymethyl methacrylate (PMMA) and the like.

The present methods may include a step of forming a contact lens in a moulding assembly, which comprises a first mould part and a second mould part assembled together. In the case of hydrogel lenses or silicone hydrogel lenses, the lenses can be made by polymerizing a hydrogel or silicone hydrogel lens formulation that includes a polymerization initiator in a lens shaped cavity formed between the first mould part and the second mould part. For silicone elastomer lenses, the lenses can be made by curing, vulcanizing, or catalysing, such as by hydrosylation, a liquid silicone elastomer material in a lens shaped cavity formed between the first mould part and the second mould part. The surface of each mould part that forms the contact lens shaped cavity may be convex, concave, planar or a combination of thereof. After formation of the contact lens, the two mould parts are separated such that the contact lens remains attached to the surface of one of the mould parts. As a result, a contact lens is provided on a surface of the first or second mould part. In some other embodiments, it may be desirable to place the lens member on a surface of a mould part that was not used to produce the first lens member, but that may require additional steps to achieve the desired alignment of the member to the mould part. The lenses may then be removed from the mould part to which they are attached, and further processed, such as by extraction and hydration, and inspected, and packaged in a package and sterilized.

FIG. 1 shows a contact lens 10 according to embodiments of the invention. The contact lens 10 comprises an optic zone 11 and a peripheral zone 13. The optic zone 11 comprises the part of the lens through which a wearer of the contact lens sees. The optic zone 11 forms a lens designed to provide vision correction to the wearer. The peripheral zone 13 surrounds the optic zone 11 and does not provide any vision correction to the wearer. The peripheral zone 13 may perform other functions. For example, the peripheral zone 13 may serve to help maintain the contact lens on the wearer's eye. In some embodiments of the invention, the peripheral zone 13 may include a ballast in order to maintain a predetermined orientation of the contact lens on the wearer's eye.

The two surfaces of the contact lens are shaped such that they vary across the optic zone 11 to form first and second surface power maps. The first and second surface power maps together form a lens power map. Thus, the optic zone can be said to provide a first surface power map, a second surface power map, and a lens power map. Within the optic zone the power maps may comprise one or more distinct regions. The example contact lens shown in FIG. 1 comprises a central region 15, an outer region 17, and a transition region 19. The outer region 17 surrounds the transition region 19. The transition region 19 surrounds the central region 15. The central region 15 and the outer region 17 may provide differing arrangements of lens power, such that they provide different vision corrections. The transition region 19 may serve for provide a smooth transition between the central region 15 and the outer region 17. It will be appreciated that the contact lens illustrated in FIG. 1 is provided merely as an example and that other contact lenses according to the invention may include more or fewer regions. For example, some contact lenses according to embodiments of the invention may omit the transition region, or may even comprise only a single region across the whole of optic zone 11. Other contact lenses according to embodiments of the invention may include additional regions, for example formed as concentric circles.

According to a first example embodiment of the invention, there is provided a multifocal contact lens. It will be appreciated that alternative embodiments may comprise an intraocular lens or a spectacle lens. The multifocal contact lens comprises a first surface and a second surface. In this example embodiment, the first surface comprises an outer surface of the contact lens and the second surface comprises an inner surface of the contact lens. It will be appreciated by the person skilled in the art that the outer surface is the convex surface of the contact lens adjacent to a wearer's eyelid and that the inner surface is the concave surface of the contact lens adjacent the wearer's eye.

A portion of the first surface can be said to be shaped to form a first surface power map. In this example embodiment, the portion corresponds to an optic zone of the contact lens. Thus, it can be said that a first surface of the optic zone forms the first surface power map. It will be appreciated by the skilled person that the first surface power map shows the modification to the overall contact lens power map provided by the shape of that surface. Thus, a contact lens having two surfaces (an inner surface and an outer surface) will comprise two surface power maps, the combination of which determines the overall contact lens power map.

Figure 2:
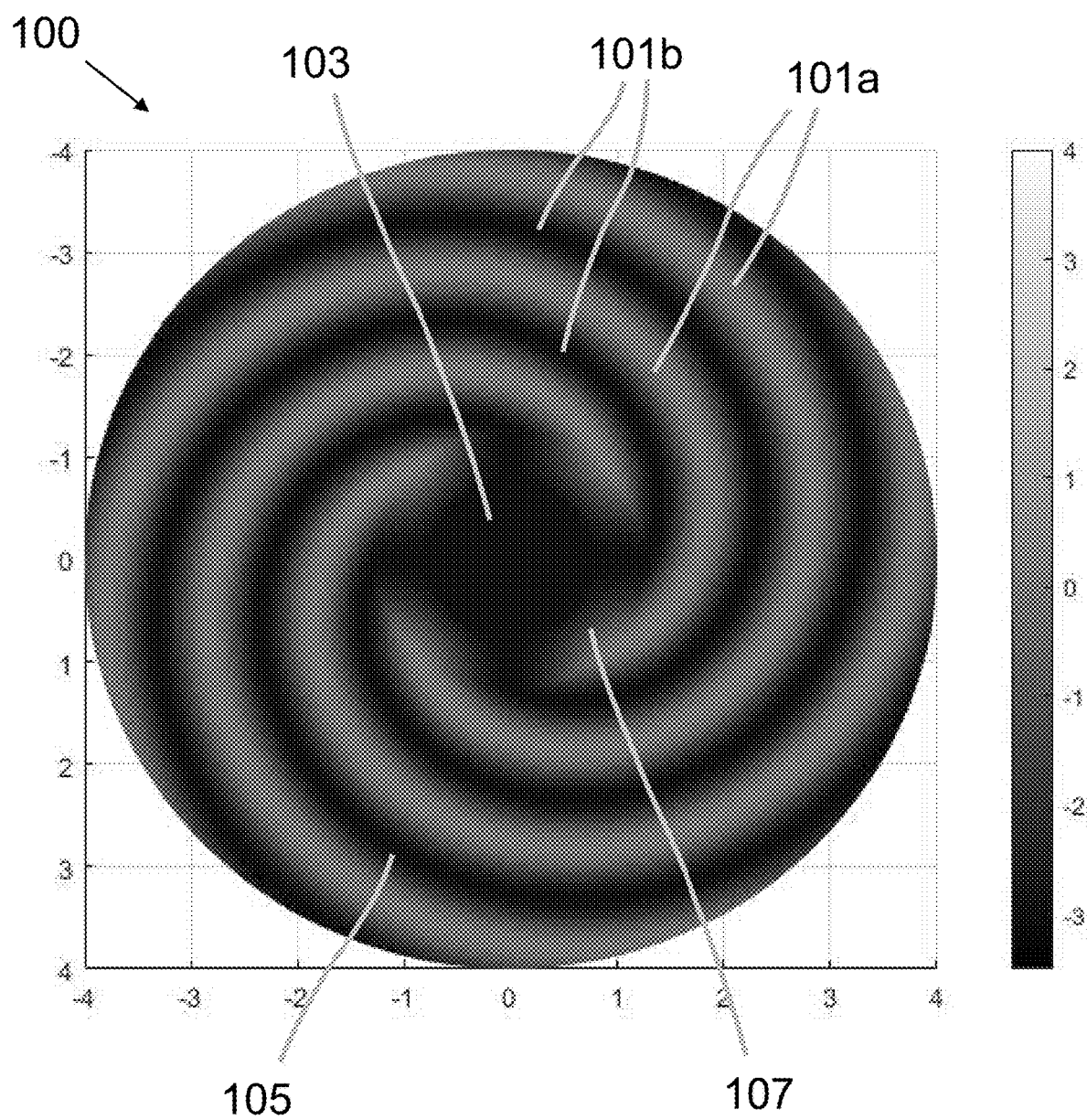
FIG. 2 shows a power map of a first surface of a portion of a contact lens according to a first embodiment of the invention.

FIG. 2 shows the first surface power map 100 of the portion of the first surface of the contact lens. The first surface power map 100 forms a spiral. The spiral comprises a plurality of (in this example 4) arms 101. Each of the arms 101 comprises one of a peak arm 101a and a trough arm 101b. It will be appreciated that a peak arm 101a is an arm which constitutes a positive excursion from the mean power of the surface power map (or the periodically varying region of the surface power map), and that a trough arm 101b is an arm which constitutes a negative excursion from the mean power of the surface power map (or the periodically varying region of the surface power map). The spiral is formed by varying the power substantially periodically both radially outwards from and angularly about an optical axis of the contact lens. It will be appreciated that an optical axis of a lens is equivalent to an optical axis of the optic zone of that lens. The power varies between a first lens power and a second lens power. The multifocal contact lens of this example embodiment has a base lens power of −3.0 D with an add power of +3.0 D. Thus, the first lens power is −3.0 D and the second lens power is +0 D. Such a contact lens may be suitable for a patient who suffers from both myopia and presbyopia. The −3.0 D base lens power provides to correct the wearer's distance vision, whilst the +3.0 D add power serves to correct for the wearer's near vision when the wearer is not able to sufficiently accommodate. It will be appreciated by a person skilled in the art that the specific values of the first lens power and the second lens power (and therefore the base lens power and add power) provided are purely examples, and that the actual values used in a given situation will be determined by the needs of the intended wearer.

In this example embodiment, the period of the radial variation is 1.2 mm and the period of the angular variation is 90 degrees. However, it will be appreciated that, in alternative embodiments, other periods of the radial and/or angular variation may be used. The period of the radial variation need only be greater than 100 microns and the period of the angular variation need only be greater than 6 degrees.

In this particular embodiment, the power varies smoothly across the first surface power map 100, substantially as a sinusoid in both the radial and angular directions. Having the surface power map vary smoothly across the portion of the lens provides for easier manufacture using a lathe of the contact lens or of apparatus (for example, a mould or an insert for a mould) for manufacturing the contact lens. However, in alternative embodiments, the power may vary according to other waveforms. For example, the power may vary as a square wave or as a rounded square wave in one or both of the radial and angular directions. Thus, in alternative embodiments, the power need not necessarily vary smoothly across the portion of the lens.

In this example embodiment, the positive and negative excursions of the sinusoid are of equal length, such that the sinusoid can be said to have a 50% duty cycle. Alternative embodiments comprise variations having other duty cycles. Thus, in such embodiments, the positive excursion may be of a different length than the negative excursion.

It will be appreciated that, the width of the arms 101 of the spiral is determined at least in part by the ratio of the period of the radial variation to that of the angular variation. In this example embodiment, each arm 101 of the spiral is approximately 500 microns wide. It will be appreciated that alternative embodiments may incorporate arms 101 having different widths. It will also be appreciated that the width of an arm 101 is defined as its perpendicular width.

Similarly, in this example embodiment, the periods of the radial and angular variations are each substantially constant across the portion. However, in alternative embodiments, the period of at least one of the radial and angular variations may change according to one or both of a radial distance from the centre of the portion and an angular position about the centre of the portion.

In alternative embodiments, the period of the angular variation is less than 180°. It will be appreciated by a person skilled in the art that the period of the angular variation determines the number of arms 101 on the spiral. Thus, in such embodiments, the spiral comprises at least two arms. It will therefore also be appreciated that certain values of angular variation, specifically those which are unit fractions of 360 degrees, may be particularly advantageous in that they allow for a surface power map without angular discontinuities.

In this example embodiment, each arm 101 of the spiral twists through an angle of 270 degrees (or 0.75 of a rotation). In alternative embodiments of the invention, each arm 101 of the spiral may twist through between a quarter of a rotation (90 degrees) and 40 rotations.

In this particular embodiment, the first surface power map 100 comprises a central region 103 and an outer region 105. The central region 103 immediately surrounds the optical axis of the contact lens. The outer region 105 surrounds the central region 103. The power of the central region does not vary periodically across the central region 103 and may, for example, be substantially constant across the central region 103. The outer region 105 comprises the spiral power map and, therefore, the angular and radial variations in power.

In alternative embodiments of the invention, each arm 101 of the spiral extends from the centre of the portion of the lens to the periphery of the portion. Thus, such embodiments do not comprise distinct central and outer regions.

As has been previously mentioned, in this example embodiment, the portion of the lens corresponds to the optic zone of a contact lens. In this example embodiment, the central region 103 has a diameter of 2 mm, which corresponds to 25% of the 8 mm diameter of the optic zone. The optic zone, through which the wearer sees, provides the first surface power map shown in FIG. 2. The contact lens may in addition comprise a surrounding peripheral zone, which provides no additional focussing or vision correction and serves merely to help maintain the contact lens in position on the wearer's eye. The diameter of the central region may be less than 25% of that of the optic zone. However, it will be appreciated that, in alternative embodiments of the invention, the diameter of the central region 103 may take other values. Similarly, it will be appreciated that the ratio of the diameter of the central region 103 to that of the optic zone may also take other values. For example, the diameter of the central region 103 may be less than 30% of that of the optic zone.

In embodiments, the central region 103 may be smaller than the minimum pupil size of a wearer of the contact lens. Such embodiments maintain multifocal vision even when the wearer's pupil constricts to its minimum size. If the central region 103 is larger than the minimum pupil size, when the wearer's pupil constricts to its minimum size, only the central region 103 will be positioned across the wearer's entrance pupil. As the power of the central region 103 does not vary as a spiral across the central region 103, the lens will not provide multifocal vision for any pupil sizes smaller than the central region 103.

Advantageously, in this example embodiment, the central region 103 provides a lens power corresponding to distance vision. Generally, brighter conditions correspond to outdoors environments. Thus, the wearer's pupil is typically more constricted when outdoors than when indoors. In addition, the wearer generally has greater need for distance vision when outdoors than when indoors. Having a central region 103 with a lens power corresponding to distance vision can allow the contact lens to provide high acuity distance vision even when the wearer's pupil is constricted to its minimum size.

This example embodiment further comprises a transition region 107. The transition region 107 surrounds the central region 103. The outer region 105 surrounds the transition region 107. The power of the transition region 107 varies to provide a smooth transition between the central region 103 and the outer region 105. It will be appreciated that such a transition region 107 is not essential and therefore that alternative embodiments do not include a transition region 107. It will be appreciated that smooth, in this context, is defined as being smooth enough for the corresponding lens curvature to be reproduced by a lathe. In this example embodiment, the transition region is approximately 300 microns wide. It will, however, be appreciated that other widths of transition region may also be used.

It will be appreciated by the skilled person that the second surface of the portion of the contact lens (i.e. the second surface of the optic zone of the contact lens of this example embodiment) forms a second surface power map. In this example embodiment the second surface power map does not vary periodically across the portion. Therefore, the contact lens has a spiral lens power map. The contact lens therefore provides reduced variation in the ratio of near focussing to distance focussing as the wearer's pupil changes size.

Whilst in this example embodiment the first surface corresponds to the outer surface of the contact lens and the second surface corresponds to the inner surface of the contact lens, a person skilled in the art will appreciate that, in alternative embodiments, the first surface may correspond to the inner surface and the second surface may correspond to the outer surface. Thus, in embodiments, the inner surface comprises a surface power map forming a spiral and the outer surface comprises a substantially flat surface power map.

According to a second example embodiment of the invention, there is provided a second multifocal contact lens. A first surface of the second contact lens is identical to that of the contact lens of the first embodiment.

Figure 3:
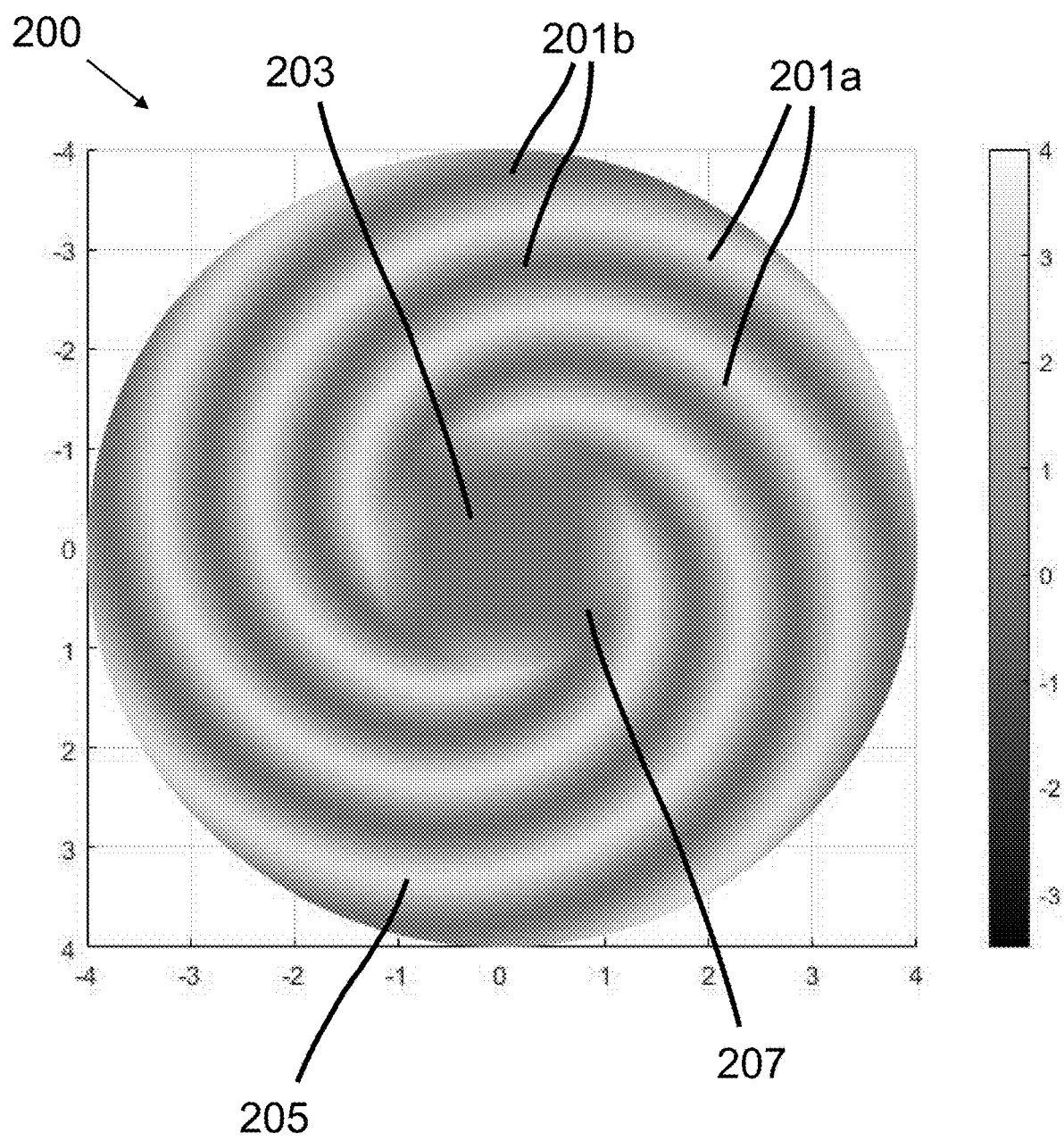
FIG. 3 shows a power map of a second surface of a portion of a contact lens according to a second embodiment of the invention.

In this embodiment, the second surface power map 200 (FIG. 3) also varies substantially periodically both angularly about and radially outwards from the centre of the portion. Thus, the second surface power map 200 also comprises a spiral. As in the case of the first surface, the spiral comprises a plurality of arms 201, including peak arms 201a and trough arms 201b. In this example embodiment, the periods of the radial and angular variations of the second surface power map 200 are the same as those of the first surface power map 100. However, a skilled person will appreciate that alternative embodiments may incorporate variations having different periods on the second surface power map 200 to one or both of those of the first surface power map 100. Once again, in alternative embodiments, the period of the angular variation of the second surface power map 200 is greater than 6 degrees. Similarly, in alternative embodiments the period of the radial variation of the second surface power map 200 may be greater than 100 microns. In this example embodiment, the second surface power map 200 also comprises a central region 203, an outer region 205, and a transition region 207.

Figure 4:
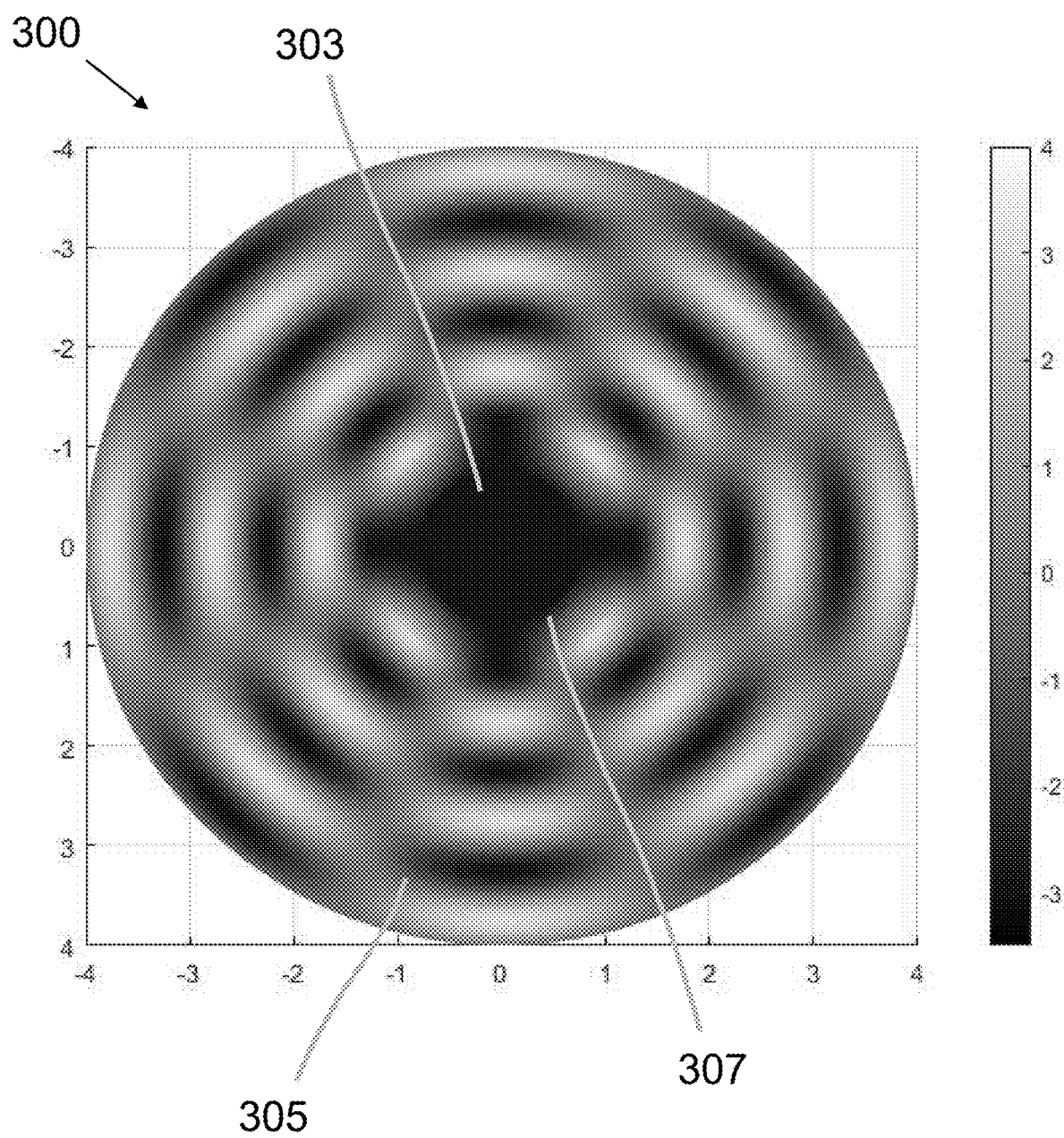
FIG. 4 shows a lens power map of the portion of the contact lens of the second embodiment.

In this example embodiment, the spiral formed by the second surface power map 200 twists in the opposite direction to that formed by the first surface power map 100 of FIG. 2. Thus, in this particular embodiment, the spirals provided by the first surface power map 100 and the second surface power map 200 are the same but for the opposing twist directions. The power map of the contact lens is determined by the superposition of the power maps of the first surface power map 100 and the second surface power map 200. FIG. 4 shows a power map of the contact lens of the second embodiment.

The superposition of the two counter-rotating spirals formed by the first surface power map 100 and the second surface power map 200 results in a lens power map which approximates a pseudo-dartboard pattern of alternating annular rings. The lens power approximately alternates between a first lens power and a second lens power in both the radial and angular directions. Because the power alternates between the first lens power and the second lens power angularly, the contact lens also provides a monotonic change in the ratio of the first lens power to the second lens power as a wearer's pupil constricts. Thus, the contact lens 300 also provides improved multifocal vision in the presence of variable light conditions.

As both the first surface power map 100 and the second surface power map 200 comprise central, peripheral, and transition regions, the overall power map of the contact lens 300 also comprises a central region 303, an outer region 305, and a transition region 307.

Figure 5:
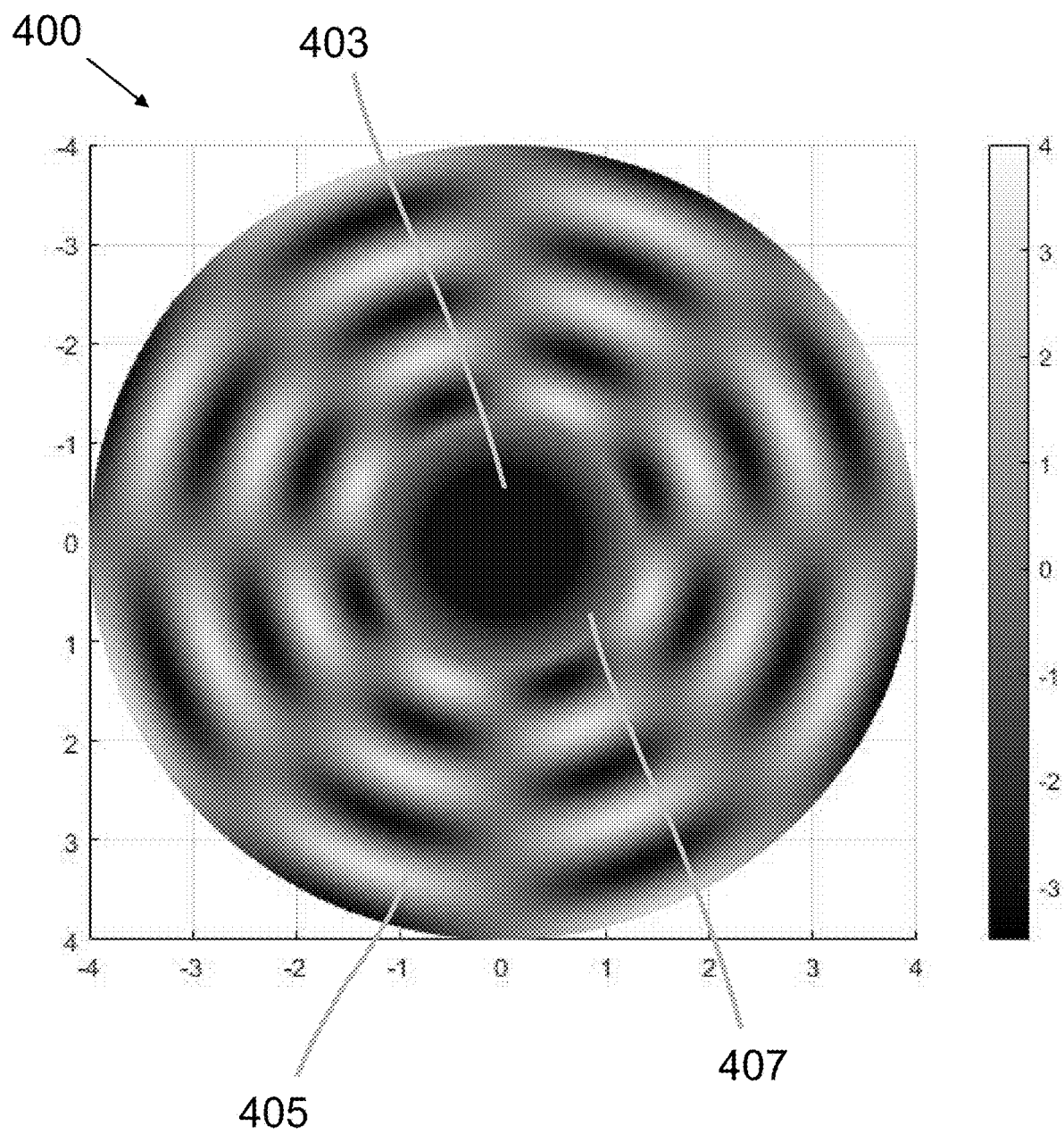
FIG. 5 shows a lens power map of a portion of a contact lens according to a third embodiment.

FIG. 5 shows a contact lens according to a third embodiment of the invention. The third embodiment is substantially the same as the second embodiment but the spiral provided by the second surface power map has been rotated through a 45 degree phase shift. As can be seen from FIG. 5, the superposition of first and second surface power maps comprising two counter-rotating spirals results in a similar pseudo-dartboard power map to that of the second embodiment. Thus, superposition of the two counter-rotating spirals results in a pseudo-dartboard lens power map irrespective of the relative phases of the first and second spirals.

Once again, the overall power map of the contact lens 400 comprises a central region 403, an outer region 405, and a transition region 407. According to a fourth embodiment of the invention, there is provided a spectacle lens. The spectacle lens comprises a spiral power map substantially as described in respect of the first embodiment of the invention. It will, however, be appreciated by the skilled person that a spectacle lens does not comprise an optic zone in the same sense as the contact lenses of the first embodiment. Therefore, in this case, the portion of the lens does not correspond to an optic zone. The skilled person will further appreciate that characteristics of the lens profile defined above in relation to the optic zone of a contact lens are similarly applicable in relation to the portion of the spectacle lens of the present embodiment. It will be appreciated that alternative embodiments of the invention comprise spectacle lenses having surface power maps substantially as described in respect of the second and third embodiments of the invention.

According to a fifth embodiment of the invention, there is provided an intraocular lens. The intraocular lens comprises a spiral power substantially as described in respect of the first embodiment of the invention. It will be appreciated that alternative embodiments of the invention comprise intraocular lenses having surface power maps substantially as described in respect of the second and third embodiments of the invention.

Figure 6:
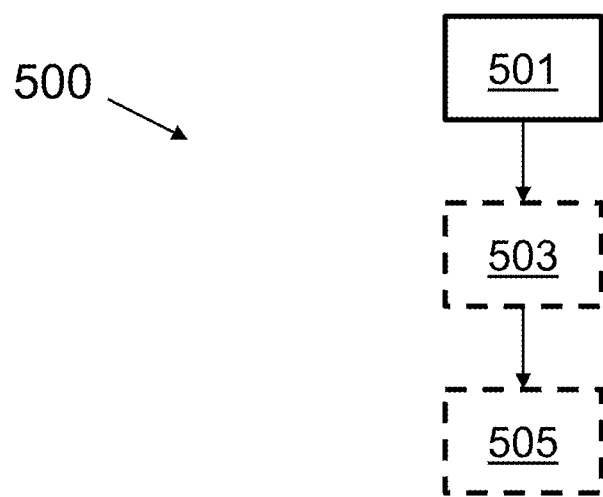
FIG. 6 shows a flow chart illustrating the steps of a method according to a sixth embodiment of the invention.

FIG. 6 shows a flow chart illustrating the steps of a method 500 of manufacturing a lens, for example a contact lens, according to a sixth embodiment of the invention.

A first step of the method 500, represented by element 501, comprises operating a lathe to shape a first surface of one of: a lens, a mould for a lens, or an insert for manufacturing a mould for a lens. The first surface is shaped such that the first surface varies across at least a portion of the lens (for example, an optic zone of a contact lens) to form a first surface power map. The first surface power map comprises a spiral and varies substantially periodically both radially outwards from and angularly about an optical axis of the contact lens. A period of the radial variation is greater than 100 microns. A period of the angular variation is greater than 6 degrees.

An optional second step of the method 500, represented by element 503, comprises operating a lathe to shape a second surface of the lens, a mould for the lens, or an insert for manufacturing a mould for the lens. The second surface is shaped such that the second surface varies across at least the portion of the lens to form a second surface power map. The second surface power map comprises a spiral and varies substantially periodically both radially outwards from and angularly about an optical axis of the contact lens. A period of the radial variation is greater than 100 microns. A period of each of the angular variation is greater than 6 degrees.

The second surface may be shaped to vary as a mirror image of the first surface. Alternatively, the second surface may be shaped such that the spiral formed on the first surface twists in the opposite direction to that formed on the second surface.

When the first surface (and the second surface where the second step 503 has been performed) are comprised on a mould for a lens or an insert for a mould for a lens, the method 500 may comprise an optional third step, represented by element 505. The third step 505 comprises using the mould of the insert for a mould for a lens to manufacture a lens.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

In the first embodiment, a lens having a spiral lens power map was provided by a first surface power map of the contact lens comprising a spiral and a second surface power map of the contact lens having substantially constant power. However, in alternative embodiments, a lens having a spiral lens power map is provided by each of the first surface power map and the second surface power map comprising a spiral. In such an embodiment, the periods and phases of the radial and angular variations of the second surface power map are the same as those of the first surface power map. Thus, the first and second surface power maps can be said to comprise mirror images of one another. The first and second surface power maps therefore superpose to form a single spiral power map and thereby a contact lens having a spiral lens power map.

In all of the first, second, and third embodiments, the surface power maps of the contact lens each comprise a central region having substantially constant power, an outer region incorporating the spiral power profile, and a transition region providing a smooth transition between the central and outer regions. However, some alternative embodiments do not incorporate a transition region. Further alternative embodiments do not incorporate distinct central and outer regions. Instead, in such embodiments, the spiral profile extends from the centre of the portion of the lens all of the way out to the radial periphery of the portion.

In the first embodiment, the spiral formed by the first surface power map twists in an anticlockwise direction. However, in alternative embodiments, the spiral formed by the first surface power map twists in a clockwise direction. In those embodiments where mirrored spirals are formed on the first and second surface power maps, the spirals may rotate in either a clockwise or an anticlockwise direction. Similarly, in the second embodiment, the spiral formed on the first surface power map twists in an anticlockwise direction and the spiral formed on the second surface power map twists in a clockwise direction. However, in alternative embodiments, the spiral formed on the first surface power map twists in a clockwise direction and the spiral formed on the second surface power map twists in an anti-clockwise direction.

In some embodiments of the invention, the spiral formed on one or both of the first and second surface power maps changes its direction of rotation at a pre-determined radial distance from the centre of the portion. For example, the spiral may rotate in a clockwise direction between the centre of the portion and the pre-determined radial distance, and in an anti-clockwise direction beyond the pre-determined radial distance. In some embodiments, the lens incorporates more than one change in the direction of rotation of the spiral. Thus, the spiral may, for example, change from a clockwise rotation to an anti-clockwise rotation before reverting to a clockwise rotation again. It will be appreciated by the skilled person that the lens can incorporate any number of changes in the direction of rotation of the spiral. It will also be appreciated that each of those changes in direction can take place at any chosen radial distance from the centre of the portion. The power map may therefore comprise annular rings alternating between clockwise and anti-clockwise rotating spirals.

In some embodiments, between regions of the ophthalmic lens having different directions of rotation, there is a region in which the power map does not vary as a spiral. For example, the region may have a substantially constant power. For example, from the centre of the portion to a first radial distance, the lens (or surface) power map may vary as a clockwise rotating spiral, followed by a region of substantially constant power, before varying as an anti-clockwise rotating spiral. The power map may therefore appear to comprise a plurality of annular rings, for example alternating between a spiral and substantially constant power, wherein the spiral regions also alternate between clockwise and anti-clockwise rotation.

Similarly, in some embodiments, the spiral may be interrupted by one or more regions, for example rings, in which the power map does not vary as a spiral. For example, the region may have a substantially constant power. Thus, for example, the power map may comprise annular rings alternating between a spiral and substantially constant power. In such embodiments, the spiral may change its direction of rotation between each interruption, or it may continue with its previous direction of rotation. Thus, the spiral may maintain a constant direction of rotation across the lens, but may be interrupted by regions of substantially constant lens power.

Whilst embodiments of the invention have been described above in relation to a method of manufacturing contact lenses, moulds for contact lenses, or inserts for moulds for contact lenses using a lathe, it will be appreciated that other methods of manufacture are also possible. In particular, the moulds or the inserts may also be manufactured using additive manufacturing techniques, for example by 3D printing.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A multifocal ophthalmic lens wherein:
a first surface of the lens varies across at least a portion of the lens to form a first surface power map;
the first surface power map comprises a spiral, with a power that varies substantially periodically both radially outwards from and angularly about an optical axis of the lens;
a period of the radial variation is greater than 100 microns; and
a period of the angular variation is a unit fraction of 360 degrees.

2. The multifocal ophthalmic lens according to claim 1, wherein:
the ophthalmic lens is a contact lens; and
the first surface varies across an optic zone of the contact lens to form the first surface power map.

3. The multifocal ophthalmic lens according to claim 1, wherein the power varies smoothly across the portion.

4. The multifocal ophthalmic lens according to claim 3, wherein the power varies both radially and angularly as one of: a rounded square wave and a sinusoid.

5. The multifocal ophthalmic lens according to claim 1, wherein the power varies both radially and angularly as a square wave.

6. The multifocal ophthalmic lens according to claim 1, wherein the periods of the radial and angular variations are each substantially constant across the portion.

7. The multifocal ophthalmic lens according to claim 1, wherein the period of at least one of the radial and angular variations changes according to one or both of: a radial distance from the optical axis of the lens and an angular position about the optical axis of the lens.

8. The multifocal ophthalmic lens according to claim 1, wherein:
the lens comprises a central region and an outer region, the central region immediately surrounding the optical axis of the lens and the outer region surrounding the central region;
the power of the central region does not vary periodically across the central region; and
the outer region comprises the angular and radial variations in power.

9. The multifocal ophthalmic lens according to claim 8, wherein the central region has a diameter of less than 50% of that of the portion.

10. The multifocal ophthalmic lens according to claim 8, wherein:
the lens comprises a transition region, the transition region surrounding the central region and the outer region surrounding the transition region; and
the power of the transition region varies to provide a smooth transition between the central and outer regions.

11. The multifocal ophthalmic lens according to claim 1, wherein:
the lens comprises a second surface which varies across the portion of the lens to form a second surface power map;
the second surface power map comprises a spiral, with a power that varies substantially periodically radially outwards from and angularly about the optical axis of the lens;
a period of the radial variation of the second surface power map is greater than 100 microns; and
a period of the angular variation of the second surface power map is a unit fraction of 360 degrees.

12. The multifocal ophthalmic lens according to claim 11, wherein:
the first surface power map and the second surface power map each comprise a spiral; and
the spirals provided by the first and second surface power maps twist in opposing directions.

13. The multifocal ophthalmic lens according to claim 11, wherein the multifocal ophthalmic lens is a myopia control lens.

14. A method of manufacturing a multifocal ophthalmic lens, the method comprising:
operating a lathe to shape a first surface of at least one of: a lens, a mould for a lens, or an insert for manufacturing a mould for a lens, such that:
the first surface varies across at least a portion of the lens to form a first surface power map;
the first surface power map comprises a spiral;
the first surface power map varies substantially periodically both radially outwards from and angularly about an optical axis of the lens;
a period of the radial variation is greater than 100 microns; and
a period of the angular variation is a unit fraction of 360 degrees.

15. The method according to claim 14, further comprising operating a lathe to shape a second surface of the lens, the mould, or the insert, such that:
the second surface varies across the portion of the lens to form a second surface power map;
the second surface power map comprises a spiral;
the second surface power map varies substantially periodically both radially outwards from and angularly about an optical axis of the lens;
a period of the radial variation is greater than 100 microns; and
a period of the angular variation is a unit fraction of 360 degrees.

16. A method of improving vision of a person, the method comprising:
providing a multifocal ophthalmic lens to a person in need of improved vision, wherein
a first surface of the lens varies across at least a portion of the lens to form a first surface power map;
the first surface power map comprises a spiral, with a power that varies substantially periodically both radially outwards from and angularly about an optical axis of the lens;
a period of the radial variation is greater than 100 microns; and
a period of the angular variation is a unit fraction of 360 degrees.

* * * * *